(12) United States Patent
Epstein

(10) Patent No.: US 6,461,361 B1
(45) Date of Patent: Oct. 8, 2002

(54) GAS-DRIVEN SPRAYING OF MIXED SEALANT AGENTS

(75) Inventor: Gordon Howard Epstein, Fremont, CA (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/302,726

(22) Filed: Apr. 30, 1999

Related U.S. Application Data

(60) Provisional application No. 60/083,854, filed on May 1, 1998.

(51) Int. Cl.$^7$ ............................................. A61M 37/00
(52) U.S. Cl. ..................... 606/82; 239/310; 222/145.2; 222/145.5
(58) Field of Search ............................ 604/82, 83, 85; 239/306, 310, 318; 222/145.1, 145.2, 145.5

(56) References Cited

U.S. PATENT DOCUMENTS

| | | | |
|---|---|---|---|
| 1,206,126 A | 11/1916 | Mitsch | |
| 3,672,544 A | * 6/1972 | Marand | 222/94 |
| 4,325,913 A | 4/1982 | Wardlaw | |
| 4,359,049 A | 11/1982 | Redl et al. | |
| 4,631,055 A | 12/1986 | Redl et al. | 604/82 |
| 4,902,281 A | 2/1990 | Avoy | 604/191 |
| 4,978,336 A | 12/1990 | Capozzi et al. | 604/82 |
| 5,116,315 A | 5/1992 | Capozzi et al. | 604/82 |
| 5,163,433 A | 11/1992 | Kagawa | 604/22 |
| 5,226,877 A | 7/1993 | Epstein | 604/35 |
| 5,368,563 A | 11/1994 | Lonneman et al. | 604/82 |
| 5,405,607 A | 4/1995 | Epstein | 424/94.64 |
| 5,474,540 A | 12/1995 | Miller et al. | 604/191 |
| 5,582,596 A | 12/1996 | Fukunaga et al. | 604/191 |
| 5,585,007 A | 12/1996 | Antanavich et al. | 210/782 |
| 5,605,255 A | 2/1997 | Reidel et al. | 222/137 |
| 5,605,541 A | 2/1997 | Holm | 604/82 |
| 5,612,050 A | 3/1997 | Rowe et al. | 424/423 |
| 5,648,265 A | 7/1997 | Epstein | 435/294.1 |
| 5,759,169 A | 6/1998 | Marx | 604/82 |
| 5,759,171 A | 6/1998 | Coelho et al. | 604/82 |
| 5,971,956 A | 10/1999 | Epstein | 604/119 |
| 5,989,215 A | 11/1999 | Delmotte et al. | 604/82 |

FOREIGN PATENT DOCUMENTS

| | | |
|---|---|---|
| DE | 81334893 | 11/1981 |
| DE | 4223356 | 7/1992 |
| DE | 19636622 | 6/1998 |
| EP | 0156098 | 12/1984 |
| EP | 0315222 | 12/1984 |
| EP | 0302411 | 7/1988 |
| EP | 0634140 | 9/1993 |
| EP | 0669100 | 2/1995 |
| EP | 0738498 | 4/1996 |
| WO | WO9531137 | 11/1995 |
| WO | WO9619940 | 7/1996 |

OTHER PUBLICATIONS

U.S. patent application Ser. No. 08/838,078, Epstein, filed Apr. 1997.
U.S. patent application Ser. No. 09/037,160, Epstein, filed Mar. 1998.

* cited by examiner

Primary Examiner—Cary E. O'Connor
(74) Attorney, Agent, or Firm—Oppenheimer, Wolff & Donnelly LLP

(57) ABSTRACT

A gas-driven spray applicator particularly suitable for spray delivery of mixed fibrin sealants for surgical use has a spray nozzle wherein droplets or a stream of mixed sealant agents are entrained in a stream of gas such as sterile compressed air. Gas entrainment of the mixed sealant overcomes problems of ineffective mixing which may occur when the sealant agents are separately discharged into overlapping spray patterns. A spray tip assembly is disclosed which is suitable for attachment to an applicator body having manually dischargeable reservoirs for the sealant agents. Clogs may be cleared by suction.

17 Claims, 10 Drawing Sheets

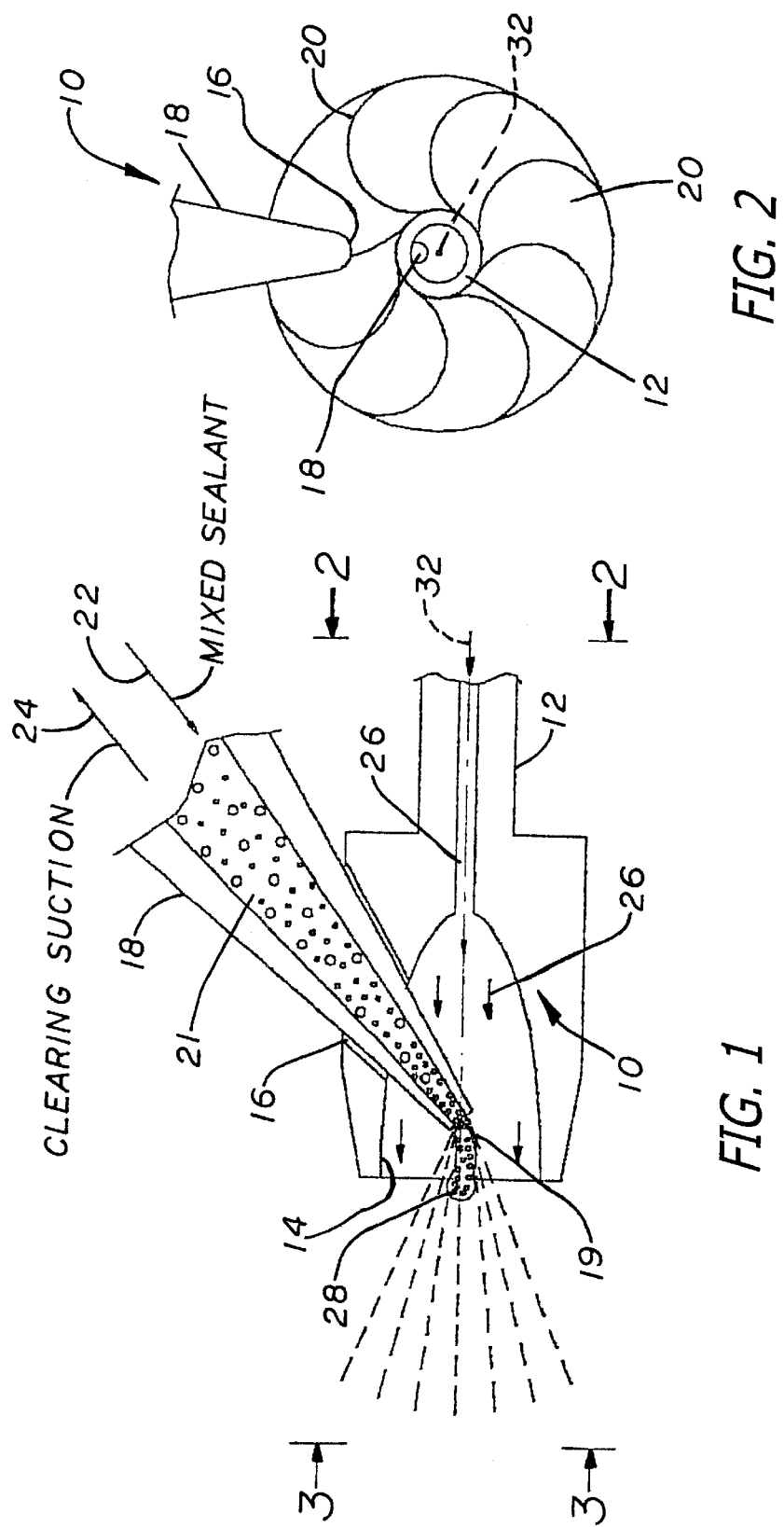

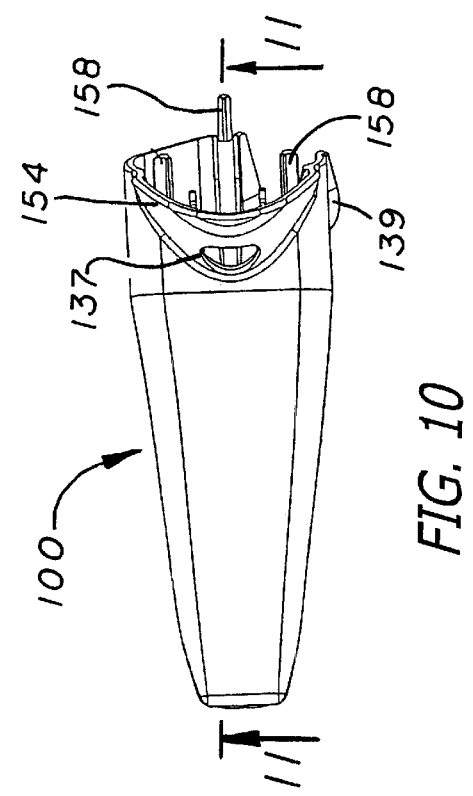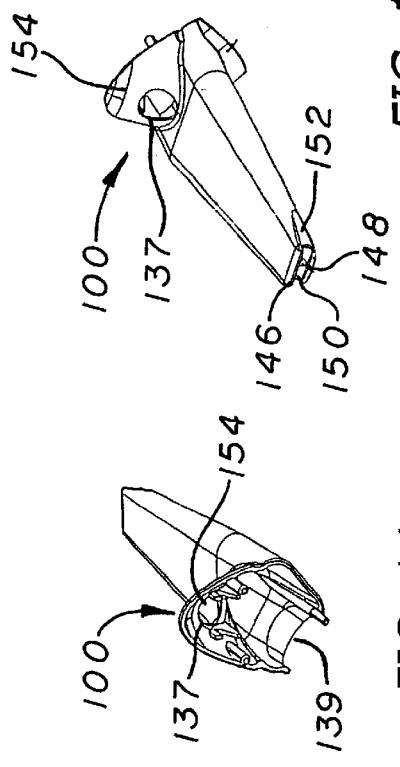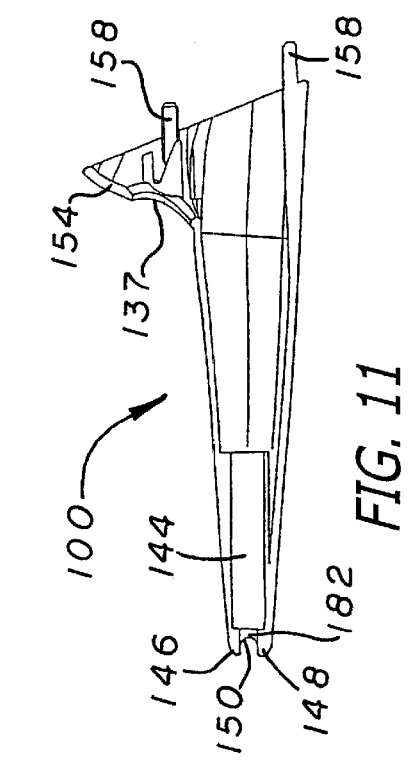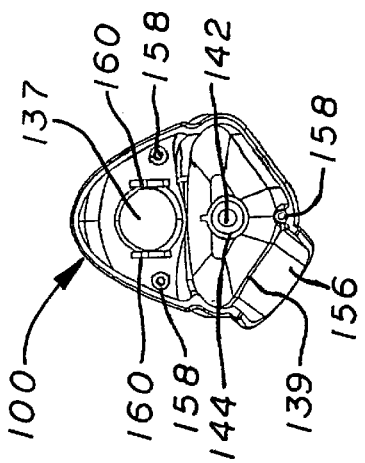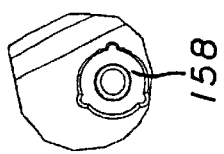

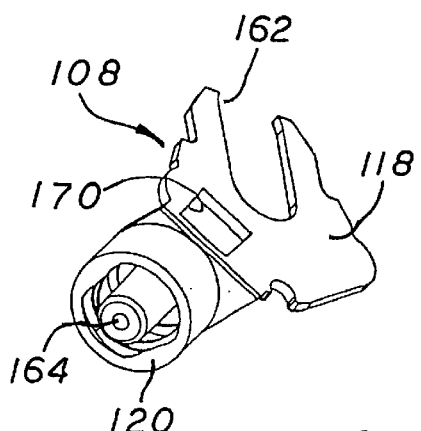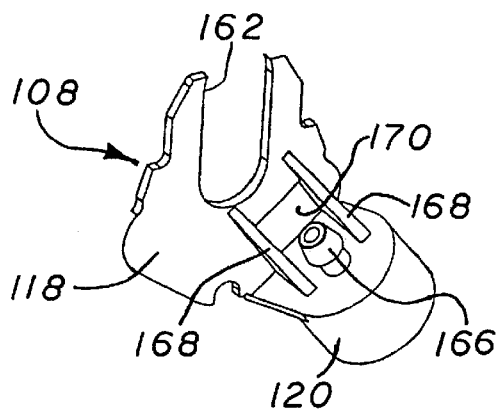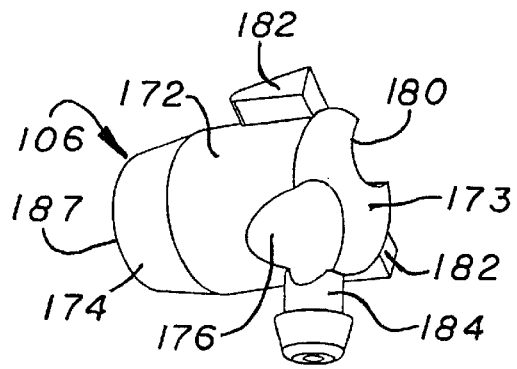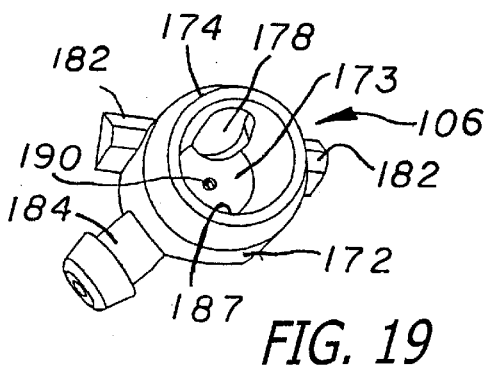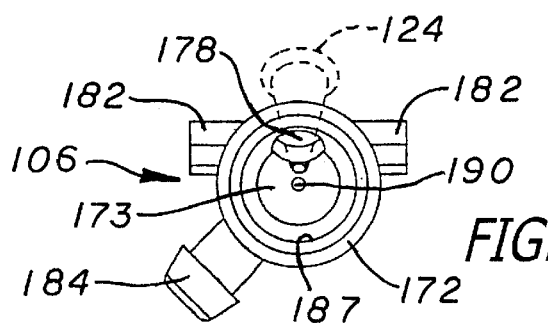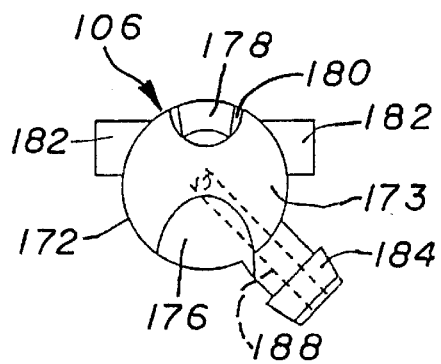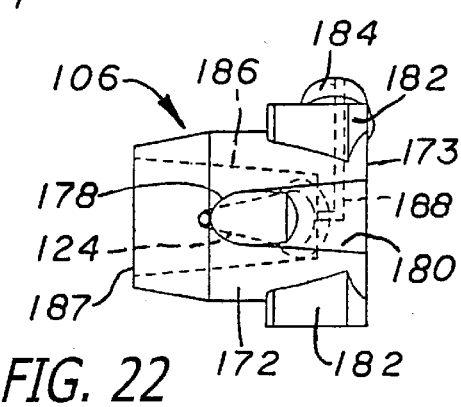

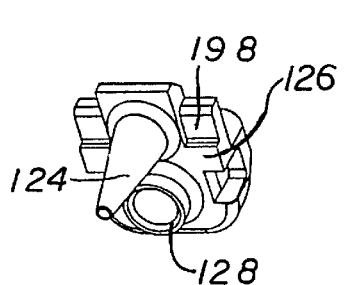
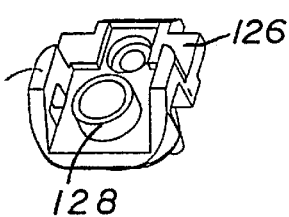
FIG. 23  FIG. 24  FIG. 25
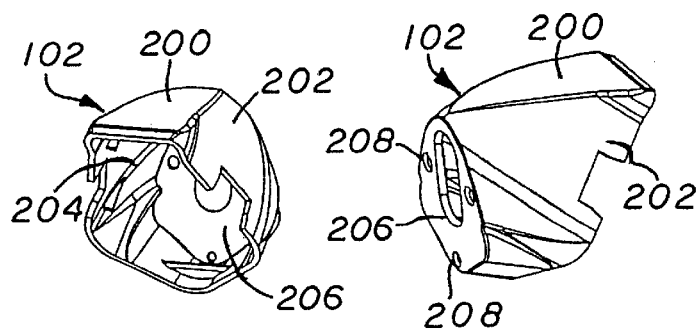
FIG. 26  FIG. 27  FIG. 28
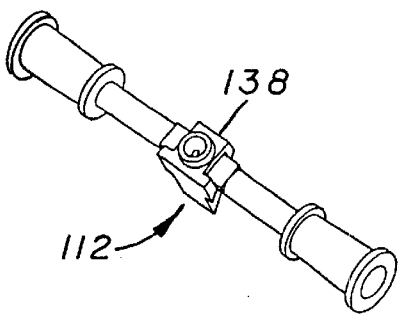
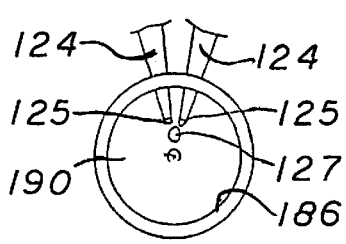
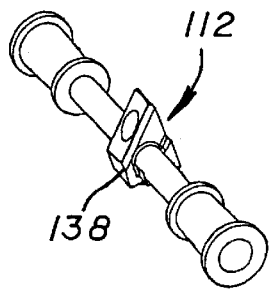
FIG. 29  FIG. 20A  FIG. 30

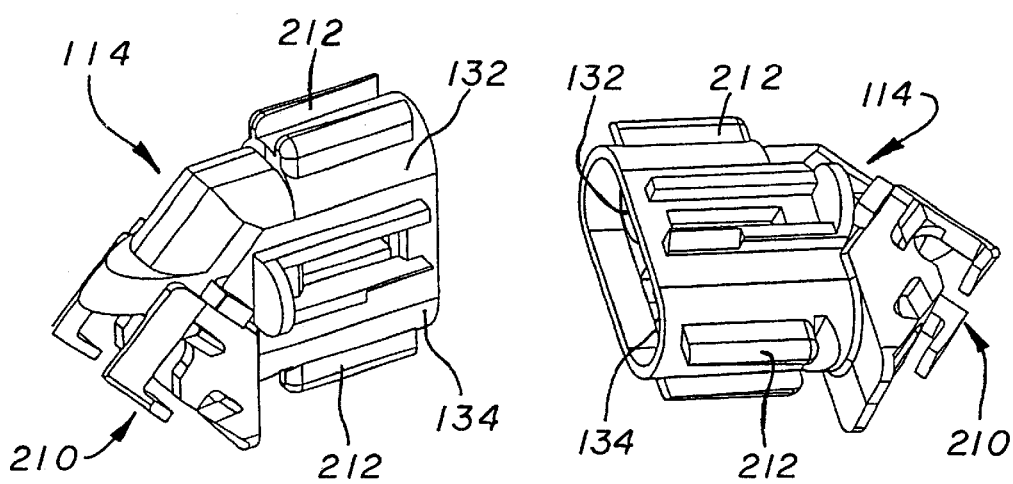
FIG. 31
FIG. 32
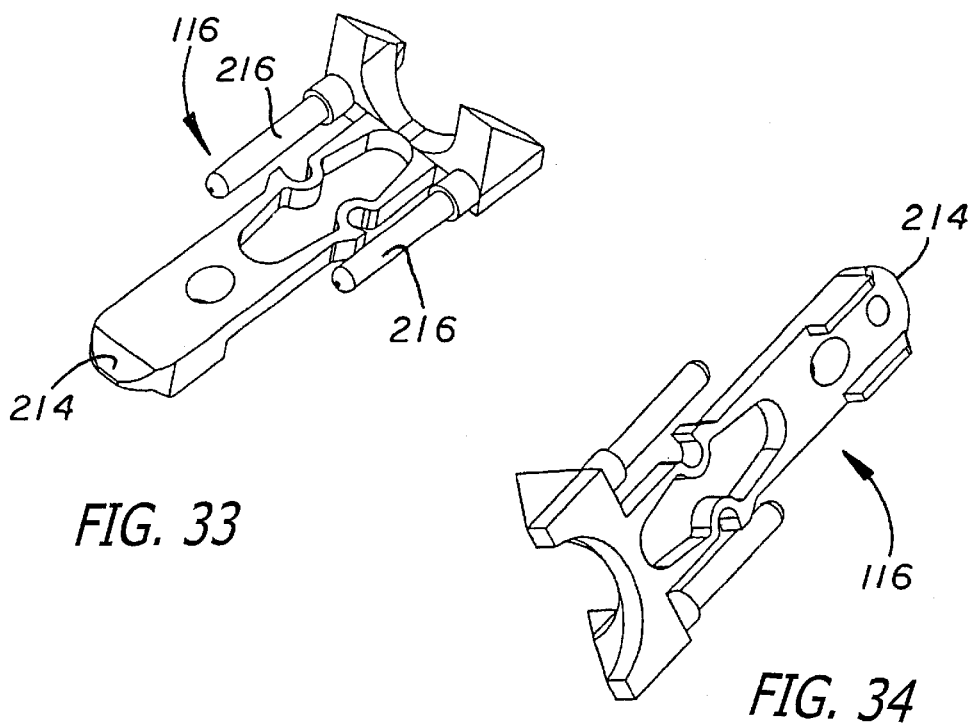
FIG. 33
FIG. 34

GAS-DRIVEN SPRAYING OF MIXED SEALANT AGENTS

This application claims the benefit of provisional application No. 60/083,854 filed May 1, 1998.

CROSS-REFERENCE TO RELATED APPLICATIONS

Continuation Status Not Claimed

This application discloses subject matter related to our copending United States patent application Ser. Nos. 08/838,078 and 08/839,614, both filed Apr. 15, 1997, to patent application Ser. No. 08/946,364 filed Oct. 7, 1997 and to patent application Ser. No. 09/037,160 filed Mar. 9, 1998 all naming Gordon H. Epstein as first inventor. The disclosures of the aforementioned United States patent applications, "the above applications" are hereby incorporated herein by reference thereto. Continuation status is not being claimed at this time. This statement is made without prejudice to applicant's right to claim continuation status at any time during copendency of the present application with respect to another application.

STATEMENT REGARDING FEDERALLY SPONSORED RESEARCH OR DEVELOPMENT (Not applicable.)

BACKGROUND OF THE INVENTION

1. Field of the Invention

The present invention relates to an applicator and method of applying multiple fluid sealant agents to a work surface and is particularly, although not exclusively, useful for applying tissue sealant agents to biological tissue to effect hemostasis or achieve other therapeutic results. More particularly, it relates to spray application of tissue sealants from a hand-held applicator.

2. Description of Related Art Including Information Disclosed under 37 CFR 1.97 and 37 CFR 1.98

Use of tissue sealants and other biological materials is an important emerging surgical technique, well adapted for the operating room or field environments such as the doctor's office or mobile medical units. Preferred sealants include fibrin sealants which are formed from blood plasma components and comprise, on the one hand, a first agent containing fibrinogen and Factor XIII and on the other hand a second agent which usually includes thrombin, and calcium ions. The fibrinogen is capable of a polymerizing and being cross-linked to form a solid fibrin clot when the agents are mixed. The necessary additional factors to simulate relevant portions of the natural blood coagulation cascade are suitably distributed between the fibrinogen and thrombin agents.

High levels of protection against transmission of infections or induction of immunological reactions can be assured by using an autologous or single-donor source for both agents. Such sealants are highly effective, are biologically degraded without residue and may promote wound healing.

Depending upon the potency of the particular formulations employed, coagulation of the sealant may take place very rapidly, yielding a gel within perhaps 10 or 20 seconds. Though often very desirable for surgical reasons, such fast-acting properties present potential problems of fouling or clogging. These problems must be overcome in devising suitable applicators, and methods of application.

A popular manually operable applicator for such two-agent sealants employs a dual syringe construction wherein two syringes, connected by a yoke, each provide a reservoir for one of the agents. In most prior devices, the sealant agents are discharged in separate streams and mixed externally of the applicator. Such applicators are similar in principle to household epoxy glue applicators commonly available in hardware stores. Achieving effective mixing externally of the applicator is problematic.

In U.S. Pat. No. 5,266,877, and the above applications, the present inventor teaches various constructions of a dual syringe applicator wherein the fluid sealant agents are mixed internally.

In one or more of the above copending applications the possibility of retrograde clearing of the mixed fluids pathway within the applicator, using suction, is also disclosed. The applicator is provided with suitable suction conduits and valving to apply suction to the work surface, to prepare it for the application of sealant, for example by removing fluids. As taught, the valving is operable to effect retrograde clearing of a sealant dispensing pathway. Enhanced mixing results and problems of fouling by deposited solids are avoided.

Such devices are useful primarily for localized tissue treatment to close wounds and the like. More widespread events, such as diffuse oozing and sealing of tissues to prevent fluid leaks, are better treated by spray applicators and a number have been proposed with varying degrees of complexity and success.

Most prior proposals for spray applicators, including applicant's own invention disclosed in a patent application Ser. No. 09/037,160 Case GE 1110, abide by the principle of external mixing because of the difficulties inherent in internal mixing. The problem of discharging a rapidly coagulating stream of mixed sealant agents through the narrow valves and orifices typically employed in spray dispensers, while preventing the applicator clogging and becoming unusable, is imposing. The problem is compounded when it is realized that such applicators are intended for occasional use: they may be used in short bursts of a few seconds each, being then set down to be used again several minutes later, providing plenty of opportunity for residual sealant to clog the applicator.

Capozzi et al. U.S. Pat. No. 5,116,315 discloses a spray applicator that outputs a mixture of two sealant agents which applicator is provided with replaceable spray orifices so that when they become clogged with sealant, the user can remove the clogged orifice and replace it with a new one. Changing the clogged orifices is inconvenient and may be difficult and inconvenient during surgery. Fibrin sealants can coagulate very quickly, in a matter of seconds. Accordingly, such a spray applicator can easily become clogged between applications if it is set down for a minute or two. The need to change the spray orifices during a surgical procedure, and to have replacement orifices available, may be quite disruptive or impractical.

Furthermore, the momentum of the spray droplets leaving the applicator is derived from manually applied pressure to the sprayed liquid. Naturally, the pressure with which the liquid is applied to the spray orifice, and therefore the momentum with which the droplets are discharged from the spray orifice, is subject to variation, caused by the mechanics of the dispensing mechanism or simple inability of a human operator to apply constant pressure throughout a range of manual movement. Accordingly with the Capozzi spray applicators, it is difficult to produce an even spray having a consistent spray pattern. It is also difficult to discharge the droplets from the applicator with a constant momentum, as would be desirable for consistent application of materials such as a surgical sealant.

Prior to the present invention, a solution to this problem has been to apply the individual sealant agents in overlapping spray patterns, with the intention that the agents will mix in the air or on the tissue surface. Thus, for example, Redl U.S. Pat. No. 4,359,049 discloses a dual syringe tissue adhesive applicator for dispensing two adhesive agents, which applicator employs a disposable mixing needle to provide a mixed sealant output a in the form of a liquid stream or a series of droplets. To provide a spray output, FIGS. 4 and 5 of Redl disclose the use of two pressurized gas streams emerging from outlets 50,51 in the region of the valves 43,44 of conveying channels 41,40 which separately supply adhesive agents from syringe bodies 1 and 2. (See column 3, lines 40–47.) Two spray patterns are generated and, according to Redl "unite at a distance of about 10 to 20 cm, rapidly forming a thin uniform adhesive film on the surface to be adhered or sealed.", see column 4 lines 1–3.

Pursuant to the present invention, it has been discovered that sealant agents discharged in separate sprays do not mix effectively. Apparently, the individual agents are frequently deposited on a work surface as individual or isolated drops or droplets that are unable to coalesce with droplets of the complementary agent. Thus mixing may be incomplete or, at best, slow. A further difficulty is that of maintaining a high degree of overlap of spatially separated sprays. Droplets deposited outside the zone of overlap are not combined with the complementary agent and therefore are not useful: valuable sealant product is wasted. Additionally, because the agents are not optimally mixed the resultant sealant may lack adhesive or cohesive strength.

There is accordingly a need for a sealant spray applicator, and method of applying a multi-agent sealant, which can effectively deliver multiple sealant agents to a work surface, for example a biological tissue, in an efficiently mixed state.

SUMMARY OF THE INVENTION

The present invention solves the problem of providing a sealant spray applicator, and method of applying a multi-agent sealant, which can effectively deliver multiple sealant agents to a work surface, for example a biological tissue, in an efficiently mixed state.

In one aspect, the invention provides a spray applicator for a liquid sealant comprising multiple sealant agents at least two of which are complementary one to the other and polymerize when mixed, the applicator comprising a sealant dispensing pathway terminating in a dispensing orifice through which the sealant agents are dispensed and a gas-entrainment chamber wherein mixed fluid sealant from the dispensing orifice is entrained in a gas stream for delivery to the work surface. Preferably a retrograde clearing device can be operated to apply suction to the sealant dispensing pathway, between applications of sealant, to remove clogs therefrom.

In another aspect the invention provides a method of spraying liquid sealant agents on to a work surface comprising mixing the liquid sealant agents in the liquid state and discharging the mixed liquid into a gas stream for dispersion of the liquid into droplets and delivery to the work surface. Optionally, the method can include a suction clearing step, between spray applications, to remove undesired deposits of mixed sealant.

By actively mixing the sealant agents prior to spraying ,the invention can assure that an effective sealant composition reaches the work surface and deposit of unmixed agents is avoided. Such active premixing is also helpful in initiating coagulation and thus providing a fast-acting sealant process. Furthermore, wasteful deposit on the work surface, of unmixed sealant agents, which will not coagulate into sealant, is avoided.

Use of a pressurized gas source to impel the spray facilitates generation of a constant velocity spray for even application of the sealant. It is difficult to obtain a steady spray by manually pressurizing of liquid sealant, as is required by conventional applicators such as those taught by Capozzi.

Preferably, although not necessarily, the sealant is a biological sealant, for example a tissue adhesive, and the work surface is a biological tissue subject to surgery. The sealant agents comprise a first, structural agent capable of gelling, and preferably of solidification and a second, activation agent which activates such gelling and, optionally, solidification. More preferably, the sealant is a tissue sealant and the first agent comprises fibrinogen and the second agent comprises, or can generate a fibrinogen activator, especially thrombin or an equivalent thereof.

BRIEF DESCRIPTION OF THE DRAWINGS

One way of carrying out the invention is described in detail below with reference to the drawings which illustrate one or more specific embodiments of the invention and in which:

FIG. 1 a schematic sectional view of a sealant spray applicator according to the invention;

FIG. 2 is a view on the line 2—2 of FIG. 1;

FIG. 3 is a view on the line 3—3 of FIG. 1, to a reduced scale showing an alternative embodiment of spray applicator;

FIG. 4 is a view similar to FIG. 3, showing another embodiment of spray applicator;

FIG. 5 is a view similar to FIG. 1 showing a still further embodiment of spray applicator having multiple gas nozzles;

FIG. 6 is a partial perspective view, partially cut away, of a still further embodiment of spray applicator;

FIG. 7 is a side elevation of another embodiment of spray applicator according to the invention, depicted in relation to a work surface;

FIG. 8 is an exploded view of a spray tip assembly, showing the individual agents of the assembly, according to a further embodiment of the invention, which spray tip assembly is intended for use with an applicator body;

FIG. 9 is a cross-sectional view of the spray tip assembly of FIG. 8, on a median plane, with the agents assembled together;

FIG. 10 is a plan view of a suction nose being a agent of a spray tip assembly shown in FIGS. 8 and 9;

FIG. 11 is a section on the line 11—11 of the suction nose shown in FIG. 10;

FIG. 12 is a righthand end elevation of the suction nose shown in FIG. 10;

FIG. 13 is an enlarged view of a detail of FIG. 12;

FIG. 14 is a distal perspective view of the suction nose of FIG. 10, to a reduced scale;

FIG. 15 is a proximal perspective view of the suction nose of FIG. 10, to a reduced scale;

FIG. 16 is a distal perspective view of a spray nose plate being a agent of the spray tip assembly shown in FIG. 8 and 9;

FIG. 17 is a proximal perspective view of the spray nose plate agent shown in FIG. 16;

FIG. 18 is an underneath side perspective view from its proximal end of a spray nozzle being a agent of the spray tip assembly shown in FIGS. 8 and 9;

FIG. 19 is an underneath perspective view, from its distal end of the spray nozzle shown in FIG. 18;

FIG. 20 is an end view, as seen in the proximal direction, of the spray nozzle shown in FIG. 18;

FIG. 20A is a schematic end view, as seen looking in a proximal direction, of an alternative embodiment wherein a spray nozzle is supplied with sealant from two lumens;

FIG. 21 is an end view, as seen in the distal direction, of the spray nozzle shown in FIG. 18;

FIG. 22 is a plan view of the spray nozzle shown in FIG. 18;

FIG. 23 is an underneath side perspective view from its distal end of an application tip being a agent of the spray tip assembly shown in FIGS. 8 and 9;

FIG. 24 is a cross-sectional view from the lefthand side on a center plane of the application tip shown in FIG. 23;

FIG. 25 is a side perspective view from above, in the distal direction, of the application tip shown in FIG. 23;

FIG. 26 is a side perspective view from its proximal end of a cover, being a agent of the spray tip assembly shown in FIGS. 8 and 9;

FIG. 27 is a side perspective view in the proximal direction, of the cover shown in FIG. 26;

FIG. 28 is a cross-sectional view from the righthand side on a center plane of the cover shown in FIG. 26;

FIG. 29 is an underneath perspective view of a manifold being a agent of the spray tip assembly shown in FIGS. 8 and 9;

FIG. 30 is a side perspective view, from above, of the manifold shown in FIG. 29;

FIG. 31 is a side perspective view in the proximal direction of a vacuum tube assembly being a agent of the spray tip assembly shown in FIGS. 8 and 9;

FIG. 32 is an underneath perspective view, from one side, of the manifold shown in FIG. 31;

FIG. 33 is a top perspective view of a shuttle valve being a agent of the spray tip assembly shown in FIGS. 8 and 9; and FIG. 34 is an underneath perspective view, of the shuttle valve shown in FIG. 33.

DESCRIPTION OF THE PREFERRED EMBODIMENTS

Figure 3:
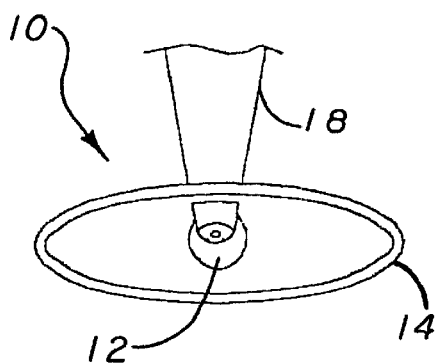
Figure 4:
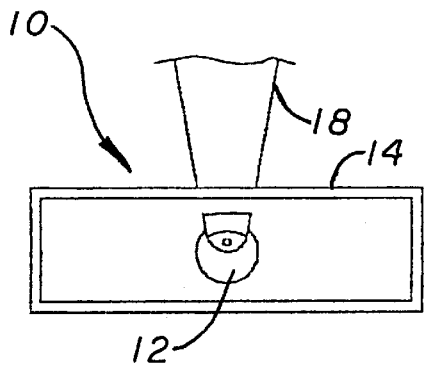
Figure 5:
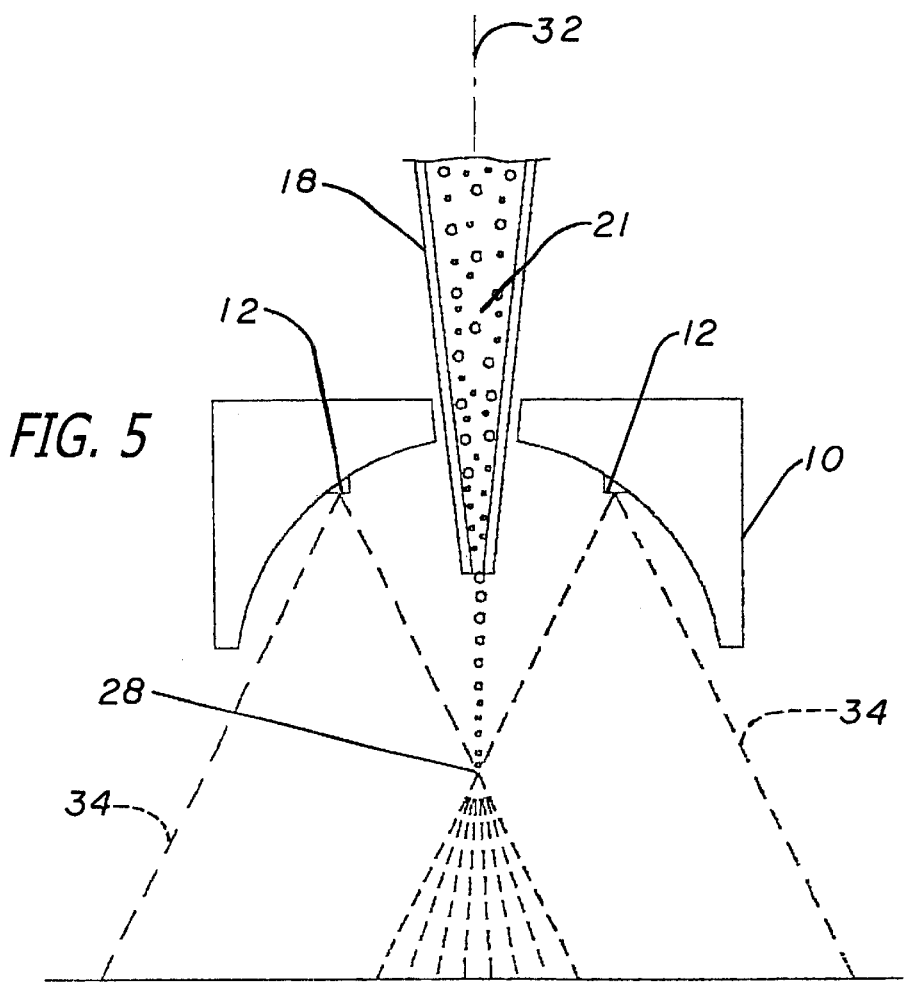

Referring to FIGS. 1 and 2 of the drawings, the sealant spray applicator shown comprises a spray hood 10 defining an outwardly diverging spray chamber 11. Spray hood 10 has a gas inlet 12, a spray discharge mouth 14 and an opening 16 in its upper wall through which extends a sealant dispensing lumen 18 terminating in a dispensing aperture 19. Dispensing aperture 19 is preferably positioned clear of the inner wall of hood 14, somewhat above the center of gas inlet 12, so that dispensed sealant 21 emerges into the heart of the gas stream. As shown in FIG. 2, spray hood 10 can optionally be formed of relatively slidable overlapping vanes 20, giving it a variable configuration.

Dispensing lumen 18 can, for example, be the dispensing lumen, referenced 106, of an embodiment of non-spray applicator such as shown and described in Epstein et al. co-pending application No. 09/037,160 filed Mar. 9, 1998, case GE 1110 (Suction aspiration lumen 110 shown in that application is not employed in the embodiment of spray applicator invention described herein.)

The novel spray applicator described herein may be adapted also to apply suction to the work surface, for example, in a manner comparable with the teaching in application 09/037,160 which employed a protruding suction nose 306 with an extensible end portion 314. Such a nose has particular utility for the present invention as a spacer to ensure that a minimum distance is maintained between the air stream from the sprayer and the patient tissue surface. This mitigates the well known risk of gas embolism which can be caused by fast-moving air too close to surgical wounds.

My prior application 09/037,160 discloses various sealant applicators comprising an applicator body provided with a pair of syringe reservoirs, for two liquid sealant agents, which agents are dispelled from the syringe reservoirs by manual pressure applied to a trigger-like actuator. The body also is fitted with a suction connection and manually operable suction control valve. A range of applicator heads or tips is mountable on to the applicator body to provide selected functionality. A mixing tip (or head) enables the two liquid agents to be discharged into a mixing chamber where they are thoroughly mixed, and provides a flow of mixed sealant out of the applicator. This flow may be the source of mixed sealant 21 shown moving down lumen 18 in the direction of arrow 22, in FIG. 1 herewith.

A preferred mixing tip also enables the operator to terminate sealant flow and apply suction to the dispensing lumen 106 or 18 in an opposite direction, shown by arrow 24 in accompanying FIG. 1, to clear it of polymerized sealant and debris. The technique may be termed "retrograde" clearing. The sealant dispensing pathway can be appropriately configured, with a non-diminishing cross-section in the clearing direction, to facilitate such clearing. Such an applicator, provided with a mixing tip and suction clearing, is preferred in the practice of the present invention.

Pressurized gas, indicated by arrows 26, is admitted through inlet 12 and travels generally in the direction of arrows 26 to emerge through mouth 14 of spray hood 10. Sealant drops 28 emerging from lumen 18 are entrained in the gas flow 26 and disperse into droplets to emerge through mouth 14 in a well-defined spray 30. Spray 30 can be applied to work surface, such as to biological tissues during animal or human surgery, by suitable positioning and movement of the spray applicator.

Because the spray droplets comprise sealant which has been thoroughly mixed prior to being dispersed into droplets, a high quality coating of sealant is deposited on the work surface in an efficient manner. Substantially all the sprayed sealant, if properly applied can be utilized, there being little or no possibility of unmixed agents being deposited on tissue. Depending upon the potency of its constituents, the sealant coagulates more or less rapidly, with good coverage and little wastage providing excellent control of sealant application. Controlling wastage is important because production of fibrin glue is expensive and, particularly in the case of a single donor or of autologous glue, only a few cc may be available.

Both the gas velocity and rate of sealant discharge are readily controlled, by suitable valves or other control structures (not shown), providing excellent management of the quality of the generated spray and the characteristics of the sealant film deposited on the work surface. Thus, for example, a very fine mist, yielding an exceptionally thin sealant coating, can be generated by carefully dispensing a small drop of sealant 21 into a relatively fast moving gas flow. Faster dispensing of sealant 21, or slower gas velocity, or both, increases the size of the sprayed droplets yielding a thicker film of sealant at the work surface.

Because gas flow 26 carries emerging sealant away from lumen 18 while it is still liquid, and sweeps the exterior of the lumen, there is little risk of external fouling of lumen 18 by accumulations of coagulating sealant.

Additionally, it is desirable to avoid fouling mouth 14 with sealant-laden spray by suitably positioning aperture 19 and, possibly, by suitable choice of the dimensions of hood 10. The smoothly curved character of the exterior surface of lumen 18 or, more specifically, its conical or frusto-conical shape is believed to assist development of a desirable air flow and "atomization" or dispersion of the dispensed liquid into minute droplets. Unlike conventional sealant sprayers which rely upon pressurized discharge of sealant agents through one or more nozzles to impart momentum to the sprayed liquid, the spray device of the present invention is not subject to problems with drips and dribbles, which can be removed by the gas stream. Switching of the gas stream on and off should be suitably coordinated with discharge of sealant from lumen 18, or the gas may flow continuously during a surgical procedure while sealant spray is discharged in short bursts from time to time. Use of retrograde suction clearing removes any liquid sealant that could be a source of such drips from lumen 18, leaving it in pristine condition between uses.

When flow of mixed sealant 21 ceases, residual sealant in lumen 18 can coagulate and clog the applicator, if left in place. By means of the invention, employing the novel applicator disclosed in the above applications, the operator can apply suction in the direction of arrow 24 to clear lumen 18 of residual sealant. Preferably such suction application is effected promptly after ceasing delivery of sealant, while residual sealant in the lumen 18 is still liquid. However the downwardly tapering shape of lumen 18 facilitates removal of solid material should any be deposited.

Alternatively, lumen 18 and any other agent contacting mixed sealant could be rendered disposable. However such disposability is less desirable than retrograde suction clearing, is inconvenient and is not compatible with frequent use of the spray applicator of the invention in a busy, stressful surgical environment.

The spray applicator of FIG. 1 provides a single coherent, pattern of spray comprising a good dispersion of well-mixed sealant droplets.

While the invention is not limited to the particular configuration shown in the drawing, and other suitable constructions will be apparent those skilled in the art, it may be seen from FIGS. 1–4 that dispensing aperture 19 of lumen 18 is disposed in the downstream half of spray chamber 11, approximately on a central axis 32 of spray chamber 11, (FIG. 1) or a little above central axis 32, to allow for the effects of gravity (FIGS. 2–4). Also aperture 19 is preferably positioned upstream of mouth 14, and does not project through mouth 14, to encourage "atomization" or good dispersion of the sealant liquid into small droplets. Furthermore, lumen 18 is preferably disposed at an angle to the direction of flow of gas stream 26 such that emerging sealant drops 28 will have a significant agent of movement in that direction and will be drawn away from lumen 18 by the gas flow. Thus, in the preferred embodiment shown in FIG. 1, lumen 18 is disposed to extend in the direction of gas flow 26 at an acute angle thereto. Such acute angle preferably is in the range of about 30 to about 60 degrees to central axis 32, more preferably in the range of about 40 to about 50 degrees.

Although hood 10 is a desirable structural feature to help guide the gas flow and control the resultant spray pattern, those skilled in the art will understand that it is not an essential feature and that gas inlet 12, or other suitable nozzle, can discharge gas freely pass lumen 18 dispersing sealant drops 28 into a desired spray.

If desired, a switching control may be provided for gas stream 26 and, in a preferred embodiment, this control is integrated with suction control means for the applicator whereby gas flow is terminated when suction is applied, in a single manipulation. Alternatively, the gas stream can be controlled in a coordinated manner with the dispensing actuator such that gas flows only when liquid sealant is being driven out of the application lumen 18.

Gas flow 26 can be provided by any suitable source, for example, by a building compressed air supply, by gasses commonly available in the operating room, by a more or less portable tank or cylinder of compressed gas, or in a particularly desirable embodiment for field applications, by a small cylinder mounted on or in the spray applicator. The gas flow is preferably clean, filtered, and sterile and may comprise air, nitrogen, carbon dioxide or other inert gas, or may comprise a special-purpose gas stream which is for example, oxygen-enriched air, or carries medications or conditioners not readily incorporated in the sealant flow. If desired, the gas flow could also provide temperature-conditioning, or humidity control, or both.

The shape of mouth 14 of spray hood 10 will usually determine the shape of a spray pattern deposited on a plane surface disposed parallel to mouth 14, or generally parallel to mouth 14, if mouth 14 is non-planar. Accordingly, the shape of mouth 14 is selected to provide a desired spray pattern. As shown, spray hood 10 preferably has a varying circular cross-section perpendicularly to the paper referring to FIG. 1, and is thus selected to be generally symmetrical about central axis 32 (opening 16 and the presence of lumen 18 being ignored for the purposes of this description). The inner walls of spray hood 10 are approximately parabolic, which is believed to be a helpful shape for projecting a suitably focused spray pattern. Clearly, the angle subtended by spray pattern 30 at its source, droplet 28 or applicator 19, is determined by a number of factors, including the particular dimensions of spray hood 10 and also the velocity of gas stream 26. Accordingly, the invention provides, as an optional feature, a regulator for the gas stream 26 enabling an operator to increase or decrease the width of spray pattern 30 by increasing or decreasing, respectively, the gas flow rate.

The approximately circular pattern of spray generated by the spray hood 10 depicted in FIGS. 1 and 2 is a useful, general-purpose shape. FIGS. 3 and 4 depict alternative configurations of spray hood 10 wherein mouth 14 has an elongated elliptical (FIG. 3) or rectangular (FIG. 4) shape which is useful for generating a wide swathe of spray 30. Other useful shapes will be apparent to those skilled in the art.

In the embodiment of FIG. 5 a multiplicity of gas nozzles is arranged around the lumen 18. Nozzles 12 all have jets (not shown) such that they each emit a divergent gas stream, typically conical which gas streams converge on the axis 32 of the applicator where they impinge upon droplets or a stream of mixed sealant: 21 dispensed from lumen 18 dispersing the droplets into spray pattern that 30. Gas nozzles 12 can be selected in combination with suitable pressures to provide an air curtain 34 around spray pattern 30 to contain the spray and define the pattern.

The number of gas nozzles 12 may range from three to twelve or even twenty, or more, and optionally they may be driven by a fluidics motor 36 enabling the nozzles to be individually switched in sequence at high-speed to provide a desired spray pattern, or to compensate for the orientation of the applicator.

As referenced above, the sealant is preferably a tissue sealant or adhesive, and comprises two components or agents one agent of which contains fibrinogen and the other agent of which contains, or can generate, thrombin. The fibrinogen and thrombin agents can each or both be derived from pooled sera, a single donor or other human source, or may be autologous, according to regulatory requirements and patient needs or preferences. Additionally the thrombin agent may be derived from animal sources, bovine thrombin being commercially available and ovine and porcine being possible alternative sources. However, human sources are preferred with single donor and autologous sources being most preferred.

One method of preparing suitable tissue sealant agents from blood plasma is described in Epstein U.S. Pat. Nos. 5,226,877, 5,405,607 and 5,648,265. Another method is described in Sierra United States provisional patent application Ser. No. 60/077,619, the disclosure of which is also incorporated herein by reference thereto. Other methods are known to those skilled in the art.

Although reference has been made to two tissue sealant agents, it will be understood that three or more agents could be employed to provide the mixed sealant 21, and other agents such as therapeutic, indicator, conditioner, or other agents can be added to or incorporated in the mixed sealant stream.

While the invention has been described in the context of generating a spray of sealant by dispensing a sealant mixture into a pressurized gaseous stream, the sealant agents may also be separately dispensed into the pressurized gaseous screen, employing known dispensing devices such for example as shown in patents numbers?, referenced above. It may be expected that dispersion and transport of the two or more liquid agents in the gaseous stream will provide a useful degree of mixing which may provide beneficial results at the work surface or may simply be a more convenient means of spray dispensing not requiring a dedicated spray applicator with dual spray heads.

Figure 6:
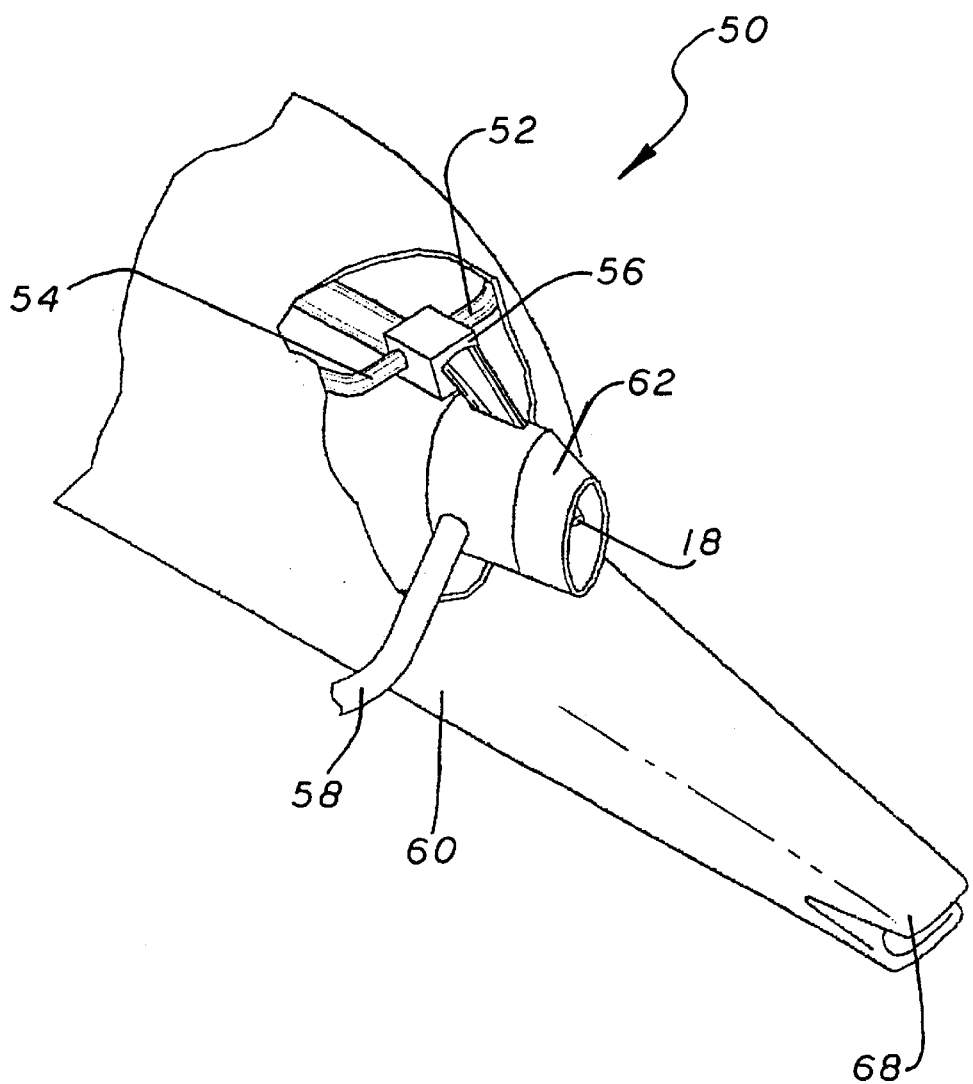

Referring to FIG. 6, a spray applicator according to invention can be embodied in a trunk-like head or tip 50 intended to be remotely attached to an applicator body, such as shown in the above-referenced application Ser. No. 09/037,160, and also in FIG. 7, (described below) which applicator body serves to dispense two streams of fluid sealant agents to conduits 52 and 54, leading to mixing head 56, where the agents are mixed and dispensed as a mixture into lumen 18. Gas is supplied by a line 58, which could be concealed within the device, from a suitable sauce, which could be a small gas tank carried in the applicator body, to a gas nozzle 60. Gas nozzle 60 is positioned to disperse sealant from a lumen 18 into a spray 62, discharging the spray from spray tip 50 through a suitably dimensioned spray port 62. Though not shown, it is preferred to provide a suitably shaped, cup-like hood within spray tip 58 whose mouth coincides with spray port 62 and which fits closely around nozzle 60 and lumen 18.

Spray tip 50 has a protruding nose 66 to serve as a spacer to maintain a desired distance from the work surface. Nose 66 is optionally fitted with an extensible portion 68 to vary that distance. Suction can be applied through an aperture or apertures 70 in nose 66 or extensible portion 68, if present, to prepare the work surface.

Figure 7:
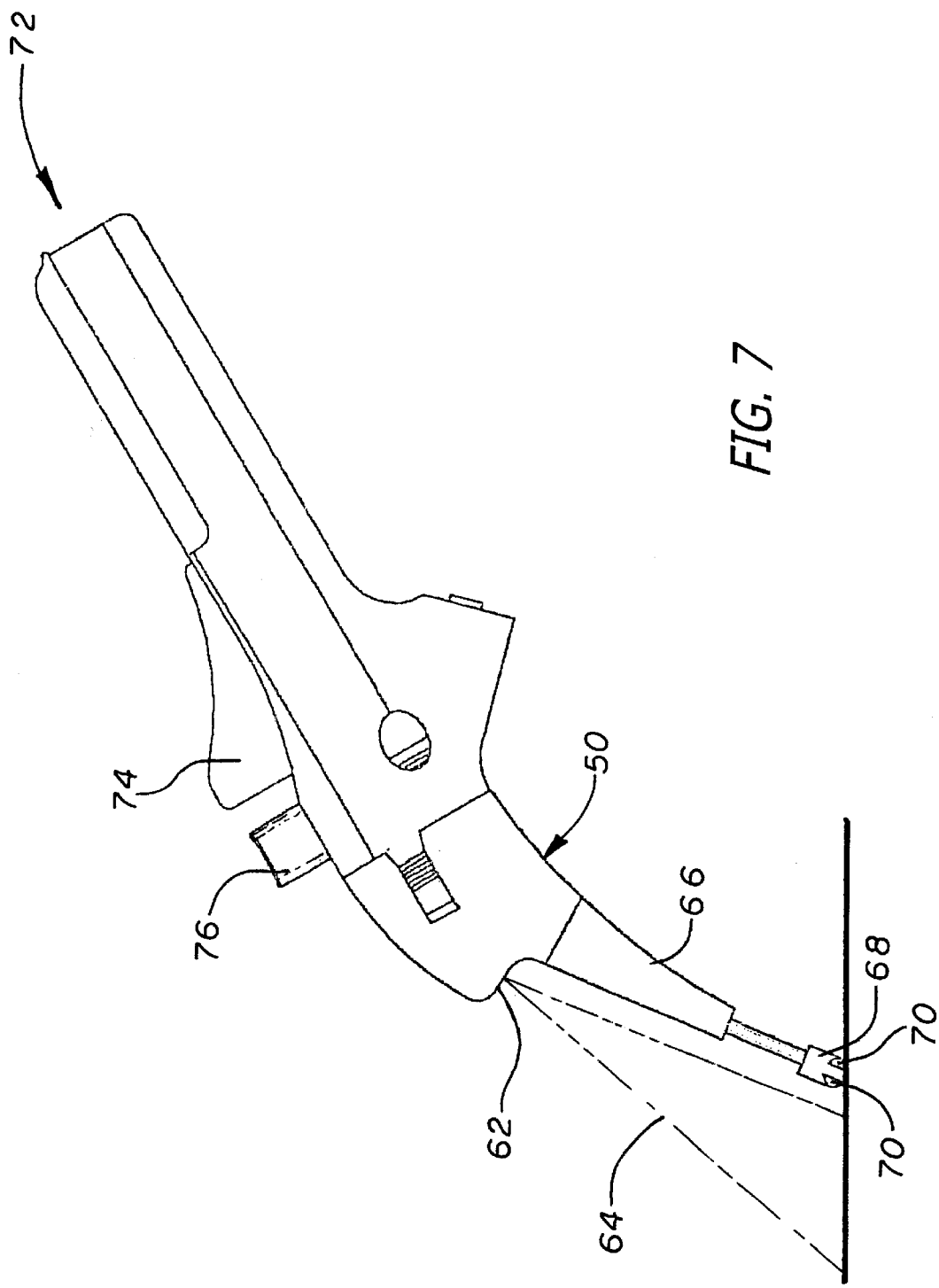

FIG. 7 shows how a spray applicator such as described in connection with FIG. 6 can be embodied in a dual agent sealant applicator with the outward appearance of that shown in FIG. 27 of application Ser. No. 09/037,160. Spray tip 50 is shown assembled with an applicator body 72 whose internal mechanism is described in that application and includes two syringe-like sealant agent reservoirs (not showed here) from which a sealant is dispensed by repeatedly pressing actuator trigger 74. Preferably, the sealant agent reservoirs are refillable.

Suction and retrograde clearing are effected by control button 76, while suction is supplied from a suitable external source via suction adapter 78. Control button 76 preferably actuates a suction valve, not shown, which balances applied suction and venting to atmosphere, permitting accurate control of suction applied to the work surface. Control button 76 preferably has an at-rest position where no suction is applied by applicator body 72, a suction-applying position where controlled suction can be applied to a work surface through an attached tip assembly and a suction clearing position where suction can be applied to a mixed sealant pathway in an attached tip assembly.

Applicator body 72 is designed to receive one or another of a range of interchangeable tips providing a variety of functions. Such tips may include a droplet tip for dispensing drops or a stream of sealant, the sealant being mixed in the tip from the two sealant agents stored in reservoirs in applicator body 72. Such tips are described in various ones of the copending application's reference herein. Alternatively the applicator tip may comprise a spray tip capable of dispensing a controlled spray of sealant, the sealant being mixed in the tip from the two sealant agents stored in reservoirs in applicator body 72. A further alternative is for the applicator tip to comprise a filler assembly from which supplies of the sealant agents may be re-filled into the reservoirs in applicator body 72.

The present invention also provides, in preferred embodiments, spray tip assemblies suitable for use with applicator body 72 and it extends to a spray applicator comprising a spray tip assembly attached to such an applicator body.

Atomizer, or impeller gas may, if desired, be provided from an on-board cylinder 82 and be controlled by actuator trigger 74, control button 76 or a separate control member (not shown). Extensible portion 68 of nose 66 acts as a feeler and is drawn, or advanced, along a work surface 80, maintaining a desired spacing while suction through ports 78 prepares the work surface and spray 64 is applied, as desired. Alternatively, suction preparation and spray application may be alternated.

Figure 8:
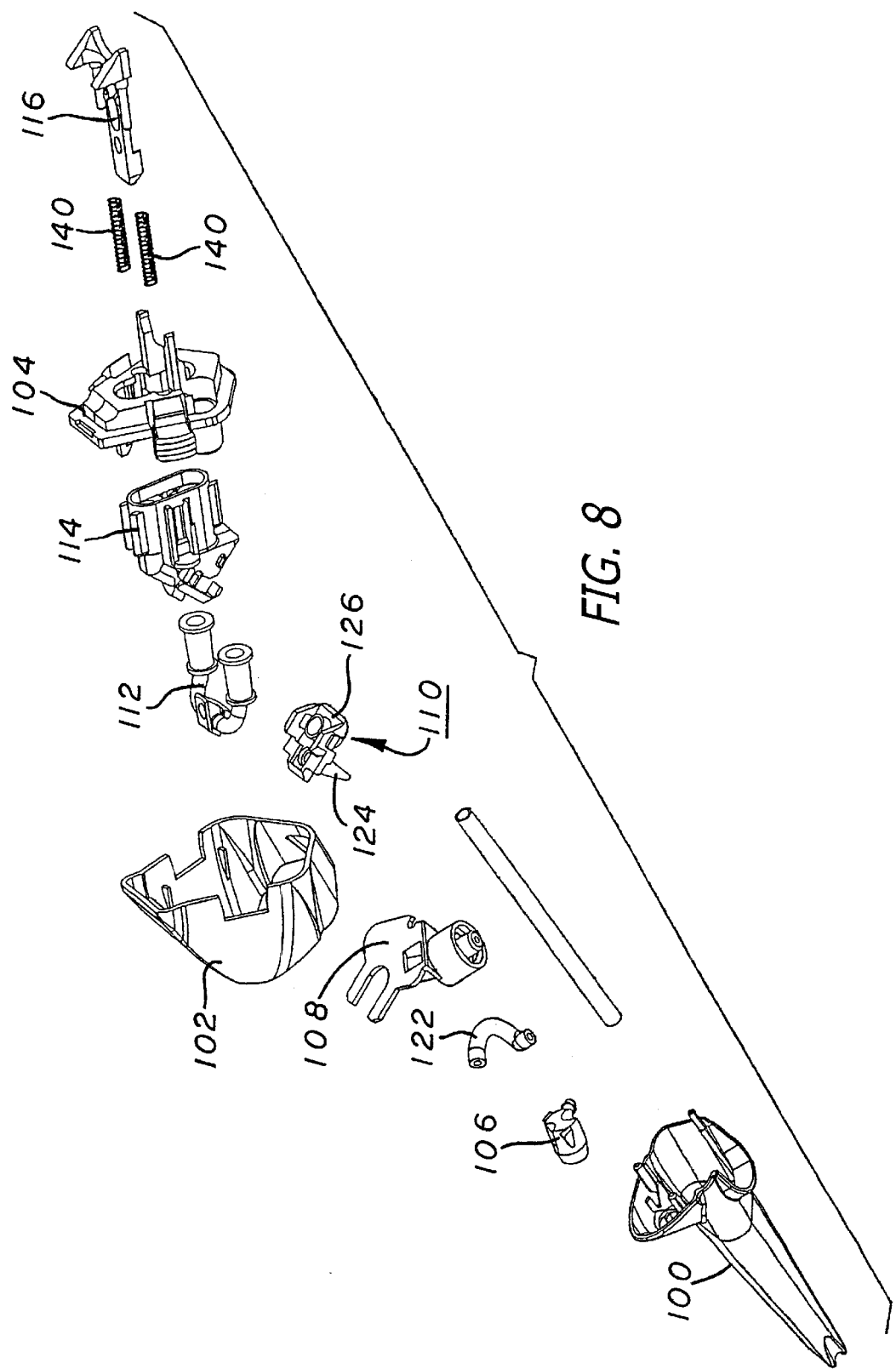
Figure 9:
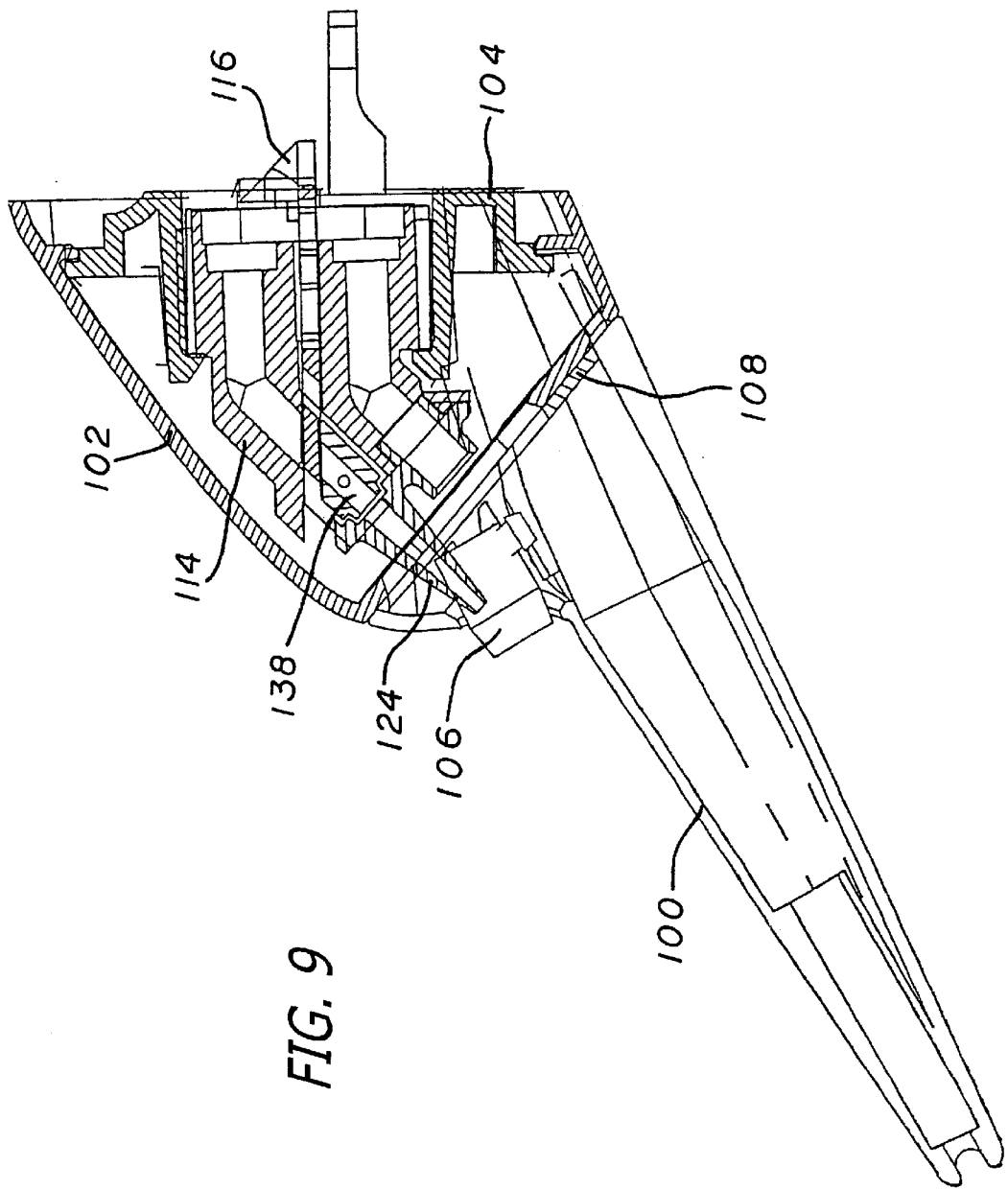

Referring now to FIGS. 8 and 9, the spray tip assembly shown is intended to provide, when attached to an applicator body such as applicator body 72, an air-driven spray applicator for dispensing a spray pattern of, for example, a mixture of two or more sealant agents which, in a preferred embodiment, are polymer and activator agents of a fibrin sealant for use in surgical procedures. The spray tip assembly comprises a suction nose 100, a cover 102 and an end plate 104 which together comprise the principal external agents of the assembly. Suction nose 100 and cover 102 which together provide the external surfaces of the spray tip assembly are configured and finished to provide an esthetic and ergonomic external shape and feel to the applicator instrument when the spray tip assembly is assembled with an applicator body such as applicator body 72. Other useful functional characteristics are also provided, as will be explained in, or apparent from, the following description. End plate 104 is engageable with cooperative structure on the applicator body to permit the spray tip assembly to be securely and releasably attached to the applicator body to receive sealant agents and controlled suction therefrom.

Supported within the assembly are a spray nozzle 106, a spray nose plate 108, an application tip 110, a manifold 112, a vacuum tube assembly 114 and a shuttle valve 116 which latter agent projects proximally through end plate 114. Spray nose plate 108 is clamped in place between suction nose 100 and cover 102 and comprises a generally diamond-shaped flat yoke 118 and a compressed air adapter 120. Yoke 118 fits around lumen 124 and suction tube 130 and locates spray nose plate 108 within the spray assembly. Air adapter 120 provides an external fitting for the connection of a compressed air line (not shown). An elbow-shaped connector tube 122, formed, for example, of silicone rubber, carries pressurized air from adapter 120 to spray nozzle 106.

Application tip 110 comprises a tapered lumen 124 which mates with manifold 112 to receive mixed sealant therefrom and discharge the sealant into nozzle 106.

U-shaped, flexible manifold 112 brings the sealant agents from applicator 72, mixes them and discharges the mixed sealant into lumen 124. Application tip 110 has a flanged base plate 126 provided with a suction connector 128, which base plate 126 matingly engages with the distal end of vacuum tube assembly 114. A suction tube 130, which may be formed, for example, of polyethylene, supplies suction from port 128, in anchor plate 126 of application tip 110, to suction nose 100.

A vacuum tube assembly 114 matingly engages with end plate 104 which end plate 104 supports and locates vacuum tube assembly 114. Vacuum tube assembly 114 is in its turn received between the arms of U-shaped manifold 112 and supports manifold 112. Vacuum tube assembly 114 has two internal suction passages arranged one above the other, namely, an upper suction clearing passage 132 and a lower suction applying passage 134. Both suction passages 132 and 134 are accessible externally of the spray tip assembly through a central opening 136 in end plate 104 where they can mate with suitably configured suction ports or connectors on applicator body 72 and be supplied with suction from a suction source in a manner controllable by the user, employing manual suction control valve 76.

Suction clearing passage 132 communicates with a mixing chamber 138 in manifold 114 to and thence with lumen 124 which is aligned to receive sealant from mixing chamber 138. Suction applying passage 134 communicates with suction tube 130 through suction port 128 in anchor plate 126, to be applied to a work surface through suction nose 100.

Shuttle valve 116, moving through vacuum tube assembly 114, acts on flexible manifold 112 to close off the supply of sealant agents from applicator body 72 and to communicate mixing chamber 138 with suction clearing passage 132, to permit retrograde clearing of lumen 124 and mixing chamber 138. Springs 140 bias shuttle valve 116 into a sealant applying position where manifold 112 is open to convey sealant agents to mixing chamber 138. In this position, shuttle valve 116 closes the top of mixing chamber 138, preventing application of suction thereto.

The agents of the suction and sealant delivery system comprised by manifold 112, vacuum tube assembly 114, end plate one of all, shuttle valve 116 and springs 140, as shown, are structurally similar to the corresponding agents of a droplet applicator tip as described in applicant's copending application Ser. No. 09/037,160, where the agent here described as vacuum tube assembly 114 is there described as lefthand and righthand clamshells 108. Cover 102 is designed to enclose and support the functional agents. The downstream agents, suction nose 100 spray nozzle 106 spray nose plate 108 and application tip 110, as well as connector tube 122 and suction tube 130 are particularly adapted for spray discharge of sealant, as opposed to delivering a sealant stream or droplets externally of the applicator tip.

In an alternative embodiment of the invention, not shown, these downstream agents could be fabricated as a separate unit to provide a readily removed functional unit adapting the sealant applicator for spraying. Similarly, the droplet applicator of the parent application could be correspondingly constructed to have those parts downstream of mixing chamber 138 fabricated as a removable unit, thus providing relatively small, interchangeable units. The agents upstream of application tip 110 could be incorporated into applicator body 72, but more preferably would be fabricated as a separate removable unit, to permit re-filling of applicator body 72 and access to internal agents for service and replacement. Suitably modified constructions of cover 102, providing enclosure and support functions, will be apparent to those skilled in the art.

Referring now to FIGS. 10–15, suction nose 100 is hollow with an elongated configuration designed for secure attachment to cover 102 at its proximal end (the righthand end as viewed in FIGS. 10 and 11) and to apply suction to a work surface at its distal end (the left-hand end as viewed in FIGS. 10 and 11). At its proximal end, suction nose 100 also has a sprayer opening 137 to receive spray nozzle 106 and a cutout 139 to accommodate a compressed air adapter element of spray nose plate 108.

At its distal end, suction nose 100 has a suction applying aperture 142 which communicates internally with a tubular socket 144 into which socket suction tube 130 is received. Externally, at the distal, suction-applying end, suction nose 100 is formed with elongated, parallel upper and lower lips 146 and 148 respectively above and below aperture 14 to which is approximately centrally located with respect to the lips 146–148. It will be appreciated that instead of a single centrally located orifice, suction aperture 142 may comprise multiple openings, or an elongated opening, located between upper lip 146 and lower lip 148.

Between lips 146 and 148, suction nose 100 comprises a channel 150 the effect of which is to recess suction aperture 142 behind lips 146-148 to deter grabbing of soft or loose work surface elements, for example tissue exposed during surgery, which might occur were suction aperture 142 to become blocked. Side vents 152 (FIG. 15) facilitate passage of work surface liquids to suction aperture 142 and also help prevent grabbing. Preferably, the distal end agents of spray nose 100 are smoothly contoured and finished so as to provide a high-quality probe suitable for engagement with and movement across surgical tissues without sharp edges, corners or molding seams that might damage, or displace, delicate tissues, or harbor infection. While lips 146 and 148 are shown in FIGS. 10, 11 and 15 as being substantially straight, they can, if desired, be smoothly curved, particularly toward their ends, where they merge into the body of suction nose 100.

As its proximal end, and on its upper surface, spray nose 100 has an upstanding cowling 154 which is formed centrally with sprayer opening 137 and is shaped to merge smoothly into cover 102. A small semi-circular wall 156 projects downwardly from the lower surface of spray nose 100 and defines cutout 139 which accommodates the compressed air adapter. Three locking posts 158, having transverse structures, for example, as shown in the enlarged view of FIG. 13 are received into cooperative openings in cover 102 enabling spray nose 100 and cover 102 to be securely assembled together. Abutments 160 can optionally be provided to guide and support spray nozzle 106 in sprayer opening 137.

The length of spray nose 100 is chosen to provide a desired spacing of spray nozzle 106 from the work surface, whereby spray nose 100 functions as a spacer as well as a suction applicator. In addition, the spacer function of spray nose 100 supplements patient safety by keeping the air stream from spray nozzle 106 at a safe distance from sensitive patient tissue which could be damaged by undue air pressure.

Referring now to FIGS. 16 and 17, yoke 118 of spray nose plate 108 is configured to be clamped snugly within suction nose 100 by cover 102 and has a U-shaped cutout 162 to accommodate sealant-dispensing lumen 124 and suction tube 130, both of which pass through yoke 118. Air adapter 120 is generally cup-shaped and projects externally through cutout 139 in suction nose 100, where it is provided with a standard fitting 164 to receive a resilient air hose. Internally of the spray tip assembly, air adaptor 120 comprises a nipple 166 to receive connector tube 122. Small buttresses 168 between yoke 118 and adapter 120 provide support and rigidity and a rectangular opening 170 in yoke 118 facilitates moldability.

Spray nose plate 108 is configured, particularly with regard to the shape of yoke 118, to have a periphery that fits closely within the proximal end of spray nose 100, providing a closing plate to spray nose 100. Spray nose plate 108 engages with the internal structure of spray nose 100, especially within cowling 154 and cutout 139, so as to fit securely and provide a solid and sturdy bearing surface for engagement with cover 102.

Referring now to FIGS. 18–22, spray nozzle 106 comprises a generally cylindrical spray body 172 which has a proximal end wall 173 and an externally tapering distal tip 174. The underside of spray body 172 has a shallow, curved recess 176 to accommodate suction tube 130 (FIG. 18). An elongated opening 178 is formed in the top wall of spray body 172 and a groove 180 is formed in end wall 173 to receive and locate lumen 124 (FIG. 19). Prism-shaped wings 182 extend either side of opening 178 and engage tightly with cooperative structure within cowling 154 on suction nose 100 to lock spray nozzle 106 in place. A flanged connector 184 projects radially from the lower side of spray body 172 to receive the other end of connected tube 122 and supply compressed air to spray nozzle 106 from air adapter 120.

Internally, spray body 172 has a spray chamber 186 (FIG. 22) which defines the spray volume where the spray originates and which opens into a mouth 187 at distal tip 174. Spray chamber 186 tapers in the proximal direction to encourage formation of a divergent or conical spray. The degree of tapering is related to the desired spray pattern and the length of suction nose 100 which controls the spacing of spray of nozzle 106 from the work surface. The cross-sectional chamber spray pattern is also largely determined by the cross-sectional shape of spray chamber 186, especially at the mouth 192 of spray chamber 186, which in the embodiment shown is circular. An air passage 188 extends through connector 184 and end wall 173 to open in an orifice 190 located in the center of end wall 173, within spray chamber 186. Lumen 124 is shown in broken lines in FIGS. 20 and 22 terminating just above orifice 190.

If desired, spray body 172 can be of variable configuration (not shown), for example it may be telescopic, to enable a user to vary the cone angle of the spray pattern generated. Thus, a wider spray, with a larger cone angle, may be generated by enlarging mouth 175 of spray body 172 or by shortening spray body 172 to bring mouth 175 closer to end wall 173. A control such as a knob, a dial or a lever can be provided to enable a user to effect such variation.

Also, spray chamber 186 may have a shape other than the cylindrical shape shown. For example, rather than a circular cross-section, spray chamber 186 may have an elliptical or other cross-sectional shape as described hereinabove or otherwise as will be apparent to those skilled in the art. Furthermore, while only one centrally disposed nozzle or orifice 190 is shown, if desired multiple orifices could be used, provided that a single gas stream emerges from spray chamber 186.

Referring to the alternative embodiment shown in FIG. 20, two lumens 124 separately deliver the sealant agents to spray chamber 186 to be discharged as a single stream of spray entrained in the gas flow emerging from gas orifice 190. Preferably, lumens 124 have tips 125 which are sufficiently spaced apart to prevent contamination of one lumen with a sealant agent from the other lumen, which could cause clogging, yet are sufficiently close together to avoid generation of one or more separate zones of a single sealant agent. More preferably, lumens 124 are disposed somewhat as shown in FIG. 20A with both tips 125 positioned a little above orifice 190 and sufficiently close together that liquid drops or streams from the two lumens merge and coalesce into a mixed droplet 127, as they descend, assuming the spray applicator to be held in an upright position with lumens 124 having the orientation shown. This being the case, the degree of merging or coalescing of the two liquids can be expected to depend upon the velocity of the gas stream emerging from orifice 190.

The invention is not limited to any particular size of apparatus or agent. However, one embodiment of spray nozzle or spray hood 10 suitable for use with a surgical sealant applicator having a body length (without spray tip assembly) of about 15 cm (6 in.) has a diameter at mouth 14 of about 5 mm (0.2 in.), with other dimensions being approximately in proportion.

Referring to FIGS. 23–25, lumen 124 depends downwardly from base plate 126 of application tip 110. Upwardly, lumen 124 communicates with mixing chamber 138 in manifold 112. Suction connector 128 projects downwardly from the underside of base plate 126 to receive suction tube 130 and projects upwardly from base plate 126 to connect with suction applying passage 134 of vacuum tube assembly 114. Arches 196 extend upwardly on either side of suction connector 128 for snap engagement with cooperative structure on vacuum tube assembly 114. Distally extending hooks (not referenced) on vacuum tube assembly 114 snap under recesses 198 on either side of lumen 124. Thus, application tip 110 is securely assembled with vacuum tube assembly 114 to receive sealant and suction therefrom, in a manner more fully described in connection with the droplet applicator shown in copending application No. 09/037,160.

Cover 102 is designed to receive application tip 110, manifold 112 and vacuum tube assembly 114 assembled together as a unit, which unit may, optionally, be mounted on plate 104 for assembly with cover 102. Externally, cover 102 is shaped to be smoothly and aesthetically contoured and finished, to be readily gripped and manipulated between the thumb and forefingers of most users and to enclose and support the just-described functional agents of the spray tip assembly. Helpful features in this respect are an upper flat 200 of limited lateral extent and adjoining side faces 202 angled to flat 200.

Internally, cover 102 has suitable support structure such as rib 204 to engage with and to support and locate vacuum tube assembly 114 and the agents assembled therewith. A flat distal end wall 206 mates cleanly with spray nose plate 108 and has small peripheral openings 208 receives posts 158 projecting of proximally from suction nose 100 permitting cover 102 to be securely attached to suction nose 100 by suitable fastening means, clamping spray nose plate 108 in place and locking spray nozzle 106 into position in cowling 154. Attachment of cover 102 to suction nose 100 is conveniently effected prior to assembly of vacuum tube assembly 114, and its accompanying agents, into cover 102.

A large central opening 208 in end wall 206 provides access to spray nozzle 106 via cutout 139 in spray nose plate 108. The underside of base plate 126 rests on yoke 118 of spray nose plate 108, with lumen 124 and suction connector 128, with suction tube 130 attached, extending through opening 208 and cutout 139. Lumen 124 extends downwardly into spray chamber 186 of spray nozzle 106 to deliver sealant thereto, while suction tube 130 applies suction to suction aperture 142 at the distal end of suction nose 100.

A compressed air stream emerging from orifice 190 entrains sealant delivered from lumen 124 and generates a mixed sealant spray which emerges from spray nozzle 106 with a pattern determined by the internal geometry of spray nozzle 106. If desired, a compressed air control (not shown) can be coupled with actuation of the sealant applicator to provide air output during sealant delivery, and stopping when sealant delivery is terminated.

FIGS. 29–34 show more details of certain components of the spray tip assembly, namely manifold 112, vacuum tube assembly 114 and shuttle valve 116. These components have generally similar structure and function to the corresponding components? described in detail in my application number 09/037,160 but differ from the corresponding components with regard to certain details, as may be seen from the respective figures.

Thus, for example, referring to FIGS. 29–30, mixing chamber 138 of manifold 112 has a generally rectangular external shape, in section, and is configured to be an accurate mating fit with base plate 126 of application tip 110 (see FIG. 25).

Referring to FIGS. 31–32, vacuum tube assembly 114 is configured to be capable of being molded in one-piece rather than in two halves Referring to FIGS. 31–32, vacuum to assembly 114 is configured to be capable of the molded in one-piece rather than in two halves, has modified manifold-engaging structure indicated generally at 210, to facilitate assembly and location of manifold 112, and has a number of longitudinal ribs, such as 212, which strengthen and locate manifold 112 with end plate 104, providing a stable construction.

Referring to FIGS. 33–34, shuttle valve 116 has a proximal nose portion 214 to function as a shock-absorbing bumper and provide an effective end stop. Side rods 216 carry compression springs 140 which resiliently bias shuttle valve 116 in the distal direction. Cam members 218, which are engaged by cooperative. structure in the applicator body to advance shuttle valve 116 distally, are connected by a cradle 220 for structural rigidity.

Other functional and structural details of these and other components of the spray the assembly will be apparent from the drawings.

The various components of the spray tip assembly shown in FIGS. 8–34 are suitable for molding from synthetic plastic materials, in most cases in the one piece shown for the given component. Some examples of suitable synthetic plastic materials are: medical grade ABS (acrylonitrile butadiene styrene), for example as supplied by Bayer AG under the trademark LUSTRAN, which may be used for suction nose 100, cover 102, spray nozzle 106 and spray nose plate 108; medical grade polycarbonate, for example as supplied by Bayer AG under the trademark MAKROLON, which may be used for end plate 104, vacuum tube assembly 114 and shuttle valve 116; and medical grade silicone, for example as supplied by Dow under the trademark SILASTIC or by Bayer AG under the trademark BAYSILONE, which may be used for manifold 112 and preferably has a durometer of 40–60 (Shore A). Other possible materials and modes of manufacture of the components will be apparent to those skilled in the art.

While illustrative embodiments of the invention have been described above, it is, of course, understood that various modifications will be apparent to those of ordinary skill in the art. Many such modifications are contemplated as being within the spirit and scope of the invention.

What is claimed is:

1. A spray applicator for spraying a liquid sealant comprising at least two sealant agents capable of coagulating when mixed together, the applicator comprising:

a) a spray hood defining a spray volume;

b) a sealant delivery pathway extending from individual sources of the at least two sealant agents to the spray volume for delivery of the at least two sealant agents to the spray volume;

c) a gas source;

d) a pressurized gas inlet to generate a gas stream into the spray volume, wherein the sealant delivery pathway can deliver the at least two sealant agents to the gas stream to generate a spray containing the at least two sealant agents; and e) a spray chamber having a mouth, the pressurized gas inlet disposed remotely from the mouth and having a sealant agent delivery region disposed between the mouth and the gas source whereby the gas stream passes through the spray volume from the gas source to the mouth and can receive and entrain the sealant agents in the delivery region;

wherein the sealant delivery pathway comprises a lumen having a sealant dispensing aperture disposed in the spray chamber in a location where the dispensing aperture is surrounded by the gas stream.

2. A spray applicator according to claim 1 wherein the sealant dispensing aperture is positioned upstream of the mouth of the spray chamber, does not project through the mouth and is disposed at an acute angle to the direction of flow of the gas stream so that sealant emerging from the dispensing aperture is drawn away from the lumen by the gas flow.

3. A spray applicator for spraying a liquid sealant comprising at least two sealant agents capable of coagulating when mixed together, the applicator comprising:

a) a spray hood defining a spray volume;

b) a sealant delivery pathway extending from individual sources of the respective sealant agents to the spray volume for delivery of the at least two sealant agents to the spray volume;

c) a pressurized gas inlet to generate a gas stream into the spray volume, wherein the sealant delivery pathway can deliver the at least two sealant agents to the gas stream to generate a spray containing the at least two sealant agents, wherein the pressurized gas inlet is connectable to a source of pressurized gas being a compressed air supply, a surgical operating room gas supply or a portable container of compressed gas; and d) a spacer element extending in the direction of spraying to maintain a desired distance between the spray volume and a work surface.

4. A spray applicator according to claim 3 comprising a suction pathway connectable with a suction source and having a suction aperture for applying suction to the work surface to be sprayed wherein the suction aperture is located in the spacer element.

5. A spray applicator for spraying a liquid sealant comprising at least two sealant agents capable of coagulating when mixed together, the applicator comprising:

a) a spray hood defining a spray volume;

b) a sealant delivery pathway extending from individual sources of the respective sealant agents to the spray volume for delivery of the at least two sealant agents to the spray volume;

c) a pressurized gas inlet to generate a gas stream into the spray volume, wherein the sealant delivery pathway can deliver the at least two sealant agents to the gas stream to generate a spray containing the at least two sealant agents; and d) a suction pathway connectable with a suction source and having a suction aperture for applying suction to a work surface to be sprayed.

6. A spray applicator for spraying a liquid sealant comprising at least two sealant agents capable of coagulating when mixed together, the applicator comprising:

a) a spray hood defining a spray volume;

b) a sealant delivery pathway extending from individual sources of the respective sealant agents to the spray volume for delivery of the at least two sealant agents to the spray volume and wherein the sealant delivery pathway comprises a mixing volume to mix the at least two sealant agents for delivery of mixed sealant to the spray volume;

c) a pressurized gas inlet to generate a gas stream into the spray volume, wherein the sealant delivery pathway can deliver the at least two sealant agents to the gas stream to generate a spray containing the at least two sealant agents;

d) a manual actuator, wherein the at least two sealant agents are delivered to the spray volume by manual operation of the manual actuator; and e) a lumen extending from the mixing volume to the spray volume, the lumen having a dispensing aperture disposed in the mixing volume for delivering the mixed sealant to the spray volume and wherein the lumen projects into the spray volume to be swept by the gas stream from the gas inlet.

7. A spray applicator for spraying a liquid sealant comprising at least two sealant agents capable of coagulating when mixed together, the applicator comprising:

a) a spray hood defining a spray volume;

b) a sealant delivery pathway extending from individual sources of the respective sealant agents to the spray volume for delivery of the at least two sealant agents to the spray volume and wherein the sealant delivery pathway comprises a mixing volume to mix the at least two sealant agents for delivery of mixed sealant to the spray volume;

c) a pressurized gas inlet to generate a gas stream into the spray volume, wherein the sealant delivery pathway can deliver the at least two sealant agents to the gas stream to generate a spray containing the at least two sealant agents;

d) a manual actuator wherein the at least two sealant agents are delivered to the spray volume by manual operation of a manual actuator; and e) a clearing device operable to clear clogged sealant material from the dispensing pathway.

8. A spray applicator according to claim 7 wherein the clearing device is connectable with the sealant dispensing pathway to apply retrograde suction to the mixing volume.

9. A spray applicator for spraying a liquid sealant comprising at least two sealant agents capable of coagulating when mixed together, the applicator comprising:

a) a spray hood defining a spray volume;

b) a sealant delivery pathway extending from individual sources of the respective sealant agents to the spray volume for delivery of the at least two sealant agents to the spray volume, wherein the sealant dispensing pathway comprises separate conduits for the least two sealant agents, each separate conduit extending from the source to the spray chamber and having a dispensing aperture located in the spray chamber to dispense a respective one of the sealant agents into the spray chamber; and c) a pressurized gas inlet to generate a gas stream into the spray volume, wherein the sealant delivery pathway can deliver the at least two sealant agents to the gas stream to generate a spray containing the at least two sealant agents.

10. A spray tip assembly intended to be attached to a spray applicator body to provide a spray applicator for spraying a liquid sealant comprising at least two sealant agents capable of coagulating when mixed, the applicator body having:

a) at least two reservoirs respectively for storing the at least two sealant agents;

b) at least two conduits for separately dispensing the at least two sealant agents; and c) a manually actuatable dispensing mechanism to discharge the sealant agents from the reservoirs through the at least two conduits;

d) at least two sealant agent receiving ports connectable with the at least two conduits;

e) a mixing chamber to receive and mix the at least two sealant agents from the at least two sealant receiving ports to provide mixed sealant;

f) a spray hood defining a spray volume;

g) a delivery conduit to receive mixed sealant from the mixing volume and deliver the mixed sealant to the spray volume;

h) a pressurized gas inlet to generate a gas stream into the spray volume; wherein the delivery conduit extends into the path of the gas stream to deliver the mixed sealant to the gas stream, to generate a spray of mixed sealant droplets; and i) a spacer element extending in the direction of spraying to maintain a desired distance between the spray volume and a work surface.

11. A spray tip assembly according to claim 10 comprising a suction pathway connectable with a suction source and having a suction aperture for applying suction to a work surface to be sprayed wherein the suction aperture is located in the spacer element.

12. A spray tip assembly intended to be attached to a spray applicator body to provide a spray applicator for spraying a liquid sealant comprising at least two sealant agents capable of coagulating when mixed, the applicator body having:

a) at least two reservoirs respectively for storing the at least two sealant agents;
 b) at least two conduits for separately dispensing the at least two sealant agents;
 c) a manually actuatable dispensing mechanism to discharge the sealant agents from the reservoirs through the at least two conduits;
 d) at least two sealant agent receiving ports connectable with the at least two conduits;
 e) a mixing chamber to receive and mix the at least two sealant agents from the at least two sealant receiving ports to provide mixed sealant;
 f) a spray hood defining a spray volume;
 g) a delivery conduit to receive mixed sealant from the mixing volume and deliver the mixed sealant to the spray volume;
 h) a pressurized gas inlet to generate a gas stream into the spray volume; wherein the delivery conduit extends into the path of the gas stream to deliver the mixed sealant to the gas stream, to generate a spray of mixed sealant droplets; and
 i) a clearing device operable to clear clogged sealant material from the dispensing pathway wherein the clearing device is connectable with the mixing volume to apply retrograde suction to clear the mixing volume and the delivery conduit.

13. A spray applicator for spraying a liquid sealant comprising at least two sealant agents capable of coagulating when mixed, the spray applicator comprising an applicator body and a spray tip assembly removably attached to the applicator body, wherein the applicator body has:

a) at least two reservoirs respectively for storing the at least two sealant agents;
 b) at least two conduits for separately dispensing the at least two sealant agents; and
 c) a manually actuatable dispensing mechanism to discharge the sealant agents from the reservoirs through the at least two conduits;

wherein the spray tip assembly has:

d) at least two sealant agent receiving ports connectable with the least two conduits;
 e) a mixing chamber to receive and mix the at least two sealant agents from the at least two sealant receiving ports to provide mixed sealant;
 f) a spray volume;
 g) a delivery conduit to receive mixed sealant from the mixing volume and deliver the mixed sealant to the spray volume; and
 h) a pressurized gas inlet to generate a gas stream in the spray volume; and wherein the delivery conduit extends into the path of the gas stream to deliver the mixed sealant to the gas stream to generate a spray of mixed sealant droplets.

14. spray applicator according to claim 13 herein the spray tip assembly comprises a spacer element extending in the direction of spraying to maintain a desired distance between the spray volume and a work surface.

15. A spray applicator according to claim 13 wherein the spray tip assembly comprises a suction pathway connectable with a suction source and having a suction aperture for applying suction to a work surface to be sprayed wherein the suction aperture is located in the spacer element.

16. A spray applicator according to claim 13 comprising a clearing device operable to clear clogged sealant material from the dispensing pathway wherein the clearing device is connectable with the mixing volume to apply retrograde suction to clear the mixing volume and the delivery conduit.

17. A spray applicator for spraying a liquid sealant comprising at least two sealant agents capable of coagulating when mixed together, the applicator comprising:

a) a spray hood defining a spray volume;
 b) a sealant delivery pathway extending from individual sources of the at least two sealant agents to the spray volume for delivery of the at least two sealant agents to the spray volume;
 c) a pressurized gas inlet to generate a gas stream in the spray volume;

wherein the sealant delivery pathway can deliver the at least two sealant agents to the gas stream to generate a spray containing the at least two sealant agents;

d) a gas source in fluid communication with the pressurized gas inlet; and
 e) a spray chamber having a mouth, the pressurized gas inlet disposed remotely from the mouth and having a sealant agent delivery region disposed between the mouth and the gas source whereby the gas stream passes through the spray volume from the gas source to the mouth and can receive and entrain the sealant agents in the delivery region;

wherein the sealant delivery pathway comprises a lumen having a sealant dispensing aperture disposed in the spray chamber in a location where the dispensing aperture is surrounded by the gas stream.

* * * * *